United States Patent
Morris et al.

(10) Patent No.: US 8,603,049 B2
(45) Date of Patent: Dec. 10, 2013

(54) ATRAUMATIC SUCTION CATHETER

(75) Inventors: Cassandra E. Morris, Roswell, GA (US); John Brewer, Marietta, GA (US); Emily A. Reichart, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 401 days.

(21) Appl. No.: 12/630,935

(22) Filed: Dec. 4, 2009

(65) Prior Publication Data

US 2010/0152707 A1    Jun. 17, 2010

Related U.S. Application Data (63) Continuation-in-part of application No. 12/335,508, filed on Dec. 15, 2008, now abandoned.

(51) Int. Cl.
*A61M 5/00* (2006.01)
(52) U.S. Cl.
USPC .......... 604/271; 604/264; 604/266; 604/267; 604/268; 604/269
(58) Field of Classification Search
USPC .......... 604/264, 266–269, 523, 271, 524–525
See application file for complete search history.

(56) References Cited

U.S. PATENT DOCUMENTS

| | | | |
|---|---|---|---|
| 2,043,630 A | 6/1936 | Raiche | |
| 2,212,116 A | 8/1940 | Eberenz | |
| 3,084,693 A | 4/1963 | Cathcart | |
| 3,158,169 A | 11/1964 | Smith | |
| 3,438,375 A | 4/1969 | Ericson | |
| 3,528,427 A | 9/1970 | Sheridan et al. | |
| 3,623,483 A | 11/1971 | Dyer, Jr. | |
| D236,920 S | 9/1975 | Sheridan | |
| 3,965,901 A | 6/1976 | Penny et al. | |
| 4,351,342 A | 9/1982 | Wiita et al. | |
| 4,490,138 A | 12/1984 | Lipsky et al. | |
| D287,166 S | 12/1986 | Lipsky et al. | |
| 4,643,712 A | 2/1987 | Kulik et al. | |
| 4,673,398 A | 6/1987 | Turner et al. | |
| D295,677 S | 5/1988 | Grimes | |
| 4,767,404 A | 8/1988 | Renton | |
| 4,775,365 A | 10/1988 | Swartz | |
| 4,863,441 A | 9/1989 | Lindsay et al. |

(Continued)

FOREIGN PATENT DOCUMENTS

CN    201139807 Y    10/2008
EP    299622 A2 *  1/1989  ............ A61M 25/00

(Continued)

OTHER PUBLICATIONS

American Society for Testing Materials (ASTM) Designation: D2240-05, "Standard Test Method for Rubber Property—Durometer Hardness," pp. 1-13, published Sep. 2005.

*Primary Examiner* — Kami A Bosworth
*Assistant Examiner* — Larry R Wilson
(74) *Attorney, Agent, or Firm* — James B. Robinson (57) ABSTRACT

There is provided a suction catheter having a tubular body with a lumen formed therethrough. The catheter has a plurality of spaced elongated apertures positioned near its distal tip. The catheter may have a fourth round opening positioned proximally to the three openings. The catheter has reduced impact force compared to similar suction catheters without the plurality of apertures near the distal tip.

8 Claims, 5 Drawing Sheets

(56) References Cited

U.S. PATENT DOCUMENTS

| | | |
|---|---|---|
| 4,894,057 A | 1/1990 | Howes |
| 5,165,420 A | 11/1992 | Strickland |
| 5,215,526 A | 6/1993 | Deniega et al. |
| 5,393,497 A | 2/1995 | Haber et al. |
| 5,514,086 A | 5/1996 | Parisi et al. |
| D372,308 S | 7/1996 | Stuart |
| D379,854 S | 6/1997 | Hirsch et al. |
| D387,162 S | 12/1997 | Zeimer et al. |
| D409,746 S | 5/1999 | Hechel |
| 5,947,988 A | 9/1999 | Smith |
| 6,106,516 A | 8/2000 | Massengill |
| 6,280,434 B1 * | 8/2001 | Kinoshita et al. ............. 604/530 |
| D469,871 S | 2/2003 | Sand |
| D487,149 S | 2/2004 | Farris |
| 6,866,655 B2 | 3/2005 | Hackett |
| D518,178 S | 3/2006 | Christiansen |
| 7,201,763 B2 | 4/2007 | Heidner |
| 7,824,345 B2 * | 11/2010 | Euteneuer et al. ............. 600/585 |
| 2002/0173816 A1 | 11/2002 | Hung |
| 2007/0219466 A1 | 9/2007 | Tremulis et al. |
| 2008/0091166 A1 | 4/2008 | Fitzgerald et al. |
| 2008/0167613 A1 | 7/2008 | Khouri et al. |
| 2009/0157002 A1 * | 6/2009 | Dumot et al. ................. 604/131 |

FOREIGN PATENT DOCUMENTS

| | | |
|---|---|---|
| EP | 1 270 038 A1 | 1/2003 |
| EP | 1 504 784 A1 | 2/2005 |
| GB | 2 441 776 A | 3/2008 |

* cited by examiner

ATRAUMATIC SUCTION CATHETER

This application is a continuation-in-part and claims the benefit of U.S. application Ser. No. 12/335,508, filed Dec. 15, 2008 now abandoned.

BACKGROUND

This disclosure concerns improved medical care for intubated patients, and more particularly to a novel suction catheter for aspiration of mucous and other fluids and secretions from at least a portion of a patient's respiratory tract, namely, the tracheobronchial passages. More particularly, this disclosure relates to suction catheters having improved tip structures which allow for more efficient suctioning of the tracheobronchial passages, while reducing the likelihood of trauma thereto during the suctioning procedure.

Suction catheters have historically consisted of a flexible plastic tube having a lumen formed in the center. They usually have had a beveled distal end or tip with an opening formed in the end which is in axial alignment with the lumen of the catheter. The proximal end of the catheter is configured to connect to a source of vacuum. A few additional openings may be provided adjacent the distal end of a suction catheter to increase its suctioning capability. These designs have continued to present problems.

When few openings are provided adjacent the distal end, they can easily become clogged when high viscosity secretions are suctioned. When the openings become completely or partially clogged, the suction force is increased at the larger, central opening at the end of the distal tip. The increased suction at the distal tip opening can result in trauma to the delicate tissue of the tracheobronchial passages if tissue of these passages is pulled against the tip during suctioning.

As a result, suction catheters with a number of openings near the distal tip have been provided to alleviate this problem. The plurality of openings may, unfortunately, act more like strainers, resulting in multiple blockages, ultimately resulting in the same traumatic damage to the tissues previously noted. It has also been found that a large number of openings near the distal tip of the catheter weakens the structure near the distal tip. This results in the catheter tip buckling and folding over on itself, making suctioning ineffective or impossible to perform due the structural failure of the tip of the suction catheter.

Alternatively, if a suction catheter is stiff and has only a few openings at or near the distal tip, the suction catheter may cause trauma upon impact with the delicate tracheobronchial tissue like that of the carina (the downward and backward projection of the last tracheal cartilage, which forms a ridge that separates the opening of the right and left main stem bronchi). This type of catheter can be advanced only with great caution by the health care provider, and may be ineffective at suctioning since it may be inserted a shorter distance into the respiratory tract of the intubated patient. There is great concern among health care providers about catheter insertion injuries even if the suction catheters are formed of more flexible materials, There remains a need for a suction catheter which effectively suctions both lower and higher highly viscosity secretions and which does not become easily blocked by such secretions. There is a need for a suction catheter which has a sufficient number of openings in and around the distal tip of the suction catheter that do not become blocked and which do not compromise the structure of the catheter. There is a need for a distal tip of a suction catheter which greatly reduces trauma due to impact against the delicate tracheobronchial tissue when suctioning.

SUMMARY

In response to the difficulties and problems discussed herein, an atraumatic suction catheter is provided. The suction catheter has a tube-shaped body with a central lumen, an outer surface and a distal tip having an opening in communication with the lumen. The proximal end has an opening in communication with the lumen and adapted to be coupled to a suction source. There is a plurality of apertures positioned near the distal tip. The ratio of the area of the apertures to the area of the outer surface of the catheter between the ends of the apertures is between 28 and 42 percent.

There are desirably three apertures and they are desirably equally spaced around the catheter. The apertures may be "racetrack" shaped as defined further below.

The suction catheter may be made from a material like a thermoplastic polyurethane elastomers, thermoplastic polyolefin elastomers, thermoplastic polyolefin block copolymers, SBS di-block elastomers, SEBS tri-block elastomers, polyvinyl chloride, polyethylene terephthalate and blends and mixtures thereof. The suction catheter desirably has a Shore hardness between 55 A and 90 A according to ASTM D2240.

Also provided herein is a suction catheter that has an impact force at least 35 percent less than a similar catheter made from the same material but having no apertures. The cross-members (between the apertures) desirably buckle outwardly upon an impact of the catheter and a surface. This applies even when the impact is not perpendicular to the surface.

DETAILED DESCRIPTION

Reference will now be made in detail to one or more embodiments, examples of which are illustrated in the drawings. Each example and embodiment is provided by way of explanation, and is not meant as a limitation. For example, features illustrated or described as part of one embodiment may be used with another embodiment to yield still a further embodiment. It is intended that the claims include these and other modifications and variations as coming within their scope and spirit.

Turning now to the drawings, as illustrated in FIGS. 1-4 and 5A-C, an atraumatic suction catheter 10 is provided. The suction catheter 10 includes a generally tubular, elongated body 12 having an opening or lumen 14 provided therethrough. A distal end or tip 16 may be beveled or formed to have a continuous curvature 44, and has a distal tip opening 18 formed therein in communication with the lumen 14. An opposite, proximal end 20 has an opening (not shown) formed therein which is also in communication with the lumen 14.

A plurality of lateral apertures (collectively "24") is provided near the distal tip 16. Each aperture 24 is desirably elongated and a perimeter 26 of each aperture 24 may desirably be formed to have parallel opposing sides 28. The perimeter 26 of each aperture 24 may also be formed to have opposing rounded ends 30 which are desirably, but not by way of limitation, U-shaped. In further discussion below, the apertures 24 having a shape with parallel opposing sides and U-shaped opposing ends shall be referred to as a "racetrack" shape. The racetrack shape may be seen, for example, in the shape of the aperture in FIG. 3.

Each of the lateral apertures 24 is desirably equally-sized and equally spaced about an outer circumference 32 of the catheter 10. That is, a center 34 of each aperture 24 is spaced to be about 120 degree angle 35 (FIG. 4) from each adjacent center 34 of each aperture 24 for embodiments having three holes. In alternative embodiments (not shown), the apertures 24 are each formed of the same size and positioned in the same position, and are of about the same length and about the same width, but are instead oval, teardrop shaped or elliptically shaped.

Each lateral aperture 24 is positioned near but a distance 36 from the distal tip 16, taken from the most distal portion of the aperture 24. Each aperture 24 may be spaced a distance 36 in a range of about 0.100 to about 0.045 inch (2.54 to about 1.14 mm) from the distal tip 16. Desirably, each aperture 24 may be spaced a distance 36 of in a range of about 0.075 to about 0.055 inch (1.91 to about 1.40 mm) from the distal tip 16. More desirably, each aperture 24 may be spaced a distance 36 in a range of about 0.070 to about 0.060 inch (1.78 to about 1.52 mm) from the distal tip 16, with a most desirable distance between the distal rounded end of the aperture 24 and the distal tip 16 of about 0.065 inch (about 1.65 mm). Alternatively, the apertures may be spaced at varying distances from the tip, however, the distance from the distal tip to the most distal portion of each aperture should not vary by more than 50 percent, desirably by not more than 25 percent and still more desirably not more than 10 percent.

Each aperture 24 may have a width 38. Each aperture 24 may have a width 38 between its elongated sides 28 in a range of about 0.110 to about 0.040 inch (2.79 to about 1.02 mm). Desirably, the width 38 between the elongated sides 28 may be in a range of about 0.100 to about 0.060 inch (2.54 to about 1.52 mm). More desirably, the width 38 between the elongated sides 28 may be in a range of about 0.090 to about 0.070 inch (2.29 to about 1.78 mm), with a most desirably width 38 of about 0.080 inch (about 2.03 mm). The sides of the apertures may also be referred to herein as "cross-members" since they span the distance between adjacent apertures 24 and it is desirable that the cross-members have a width less than 1.54 mm, though of course greater than zero, and depending on the size of the catheter and the apertures.

Each aperture 24 also has a length 42 that may be about 0.200 to about 0.160 inch (5.08 to about 4.06 mm). Desirably, each aperture 24 may have a length 42 of about 0.190 to about 0.170 inch (4.82 to about 4.32 mm). More desirably, each aperture 24 may have a length 42 of about 0.185 to about 0.175 inch (4.70 to about 4.44 mm), and most desirably a length 42 of about 0.180 inch (about 4.57 mm).

A length to width ratio may be calculated using the aperture length and width data presented above. The length to width ratio may be between 1.45 and 5, more desirably between 1.7 and 3.17 and still more desirably between 1.94 and 2.64.

The distal tip 16 may be beveled and the curvature 44 of the distal tip 16 may have a radius in a range of about 0.085 to about 0.045 inch (2.12 to about 1.14 mm). The curvature 44 of the distal tip 16 desirably has a radius of about 0.075 to about 0.055 inch (1.91 to about 1.40 mm). The curvature 44 of the distal tip 16 more desirably has a radius of about 0.070 inch to about 0.060 inch (1.78 to about 1.52 mm), and most desirably a radius of about 0.065 inch (about 1.65 mm). If the tip 16 is beveled, the distance 46 between the beginning of the curvature 44 of the distal tip 16 and the most distal point of the distal tip 16 may be in a range of about 0.070 to about 0.030 inch (1.78 to about 0.76 mm). Desirably, the distance 46 may be in a range of about 0.060 to about 0.040 inch (1.52 to about 1.02 mm). More desirably, the distance 46 may be in a range of about 0.055 to about 0.045 inch (1.40 to about 1.14 mm), and most desirably the distance 46 is about 0.051 inch (about 1.30 mm).

The perimeter 47 of the distal tip opening 18 may have a diameter within a range of about 0.110 to about 0.150 inch (2.79 to about 3.81 mm). The diameter 47 desirably may be formed within a range of about 0.120 to about 0.140 inch (3.05 to about 3.56 mm). The diameter 47 more desirably may be formed within a range of about 0.132 to about 0.123 inch (3.35 to about 3.12 mm), and most desirably the diameter 47 is about 0.128 inch (about 3.25 mm).

The body 12 of the catheter has an inner diameter 48 that may be formed within a range of about 0.110 to about 0.150 inch (2.79 to about 3.81 mm). The inner diameter 48 desirably may be formed within a range of about 0.120 to about 0.140 inch (3.05 to about 3.56 mm). The inner diameter 48 more desirably may be formed within a range of about 0.132 to about 0.123 inch (3.35 to about 3.12 mm), and most desirably the inner diameter 48 is about 0.128 inch (about 3.25 mm).

The body 12 of the catheter has an outer diameter 49 that may be formed within a range of about 0.165 to about 0.205 inch (4.19 to about 5.21 mm). The outer diameter 49 desirably may be formed within a range of about 0.175 to about 0.195 inch (4.45 to about 4.95 mm). The outer diameter 49 more desirably may be formed within a range of about 0.180 to about 0.190 inch (4.57 to about 4.83 mm), and most desirably the outer diameter 49 is about 0.188 inch (about 4.78 mm).

The inner and outer diameters will vary according to the catheter size chosen by a user as appropriate for his particular application. Catheter sizes are usually expressed as "French" and common catheter sizes range from a 5 French to an 18 French. (Note, French is a measure of circumference based on the theory that non-round tubes of the same circumference will fit into the same incision. One French is approximately 0.33 mm or 0.013 inch).

The catheter 10 also has a length 50 that may be in a range of about 25 to about 10 inches (635 to about 254 mm). Desirably, the length 50 may be in a range of about 23 to about 18 inches (584.2 to about 457.2 mm). More desirably, the length 50 may be in a range of about 22 to about 19 inches (558.8 to about 482.6 mm), and most desirably about 20.87 inches (530.1 mm). It will be understood, however, that other shorter or longer lengths may be utilized.

An aperture 52 may be provided a distance proximal to the lateral openings 24. The aperture 52 is desirably round for ease of manufacture and spaced an equal distance between two of the lateral openings 24. The aperture 52 is positioned a distance 54 from the distal tip 16 in a range of about 0.350 to about 0.500 inch (8.89 to about 12.7 mm) from the distal tip 16. Desirably, the distance 54 of the aperture 52 is about 0.400 to about 0.475 inch (10.16 to about 12.07 mm) from the distal tip 16. More desirably, the distance 54 of the aperture 52 is about 0.414 to about 0.441 inch (10.52 to about 11.2 mm) from the distal tip 16, and most desirably the distance 54 of the aperture 52 is about 0.421 inch (about 10.69 mm) from the distal tip 16.

The diameter 56 of the aperture 52 may be about 0.080 to about 0.120 inch (2.032 to about 3.05 mm) diameter. More desirably, the diameter 56 of the aperture 52 desirably may be about 0.090 to about 0.110 inch (2.29 to about 2.79 mm) diameter. Still more desirably, the diameter 56 of the aperture 52 may be about 0.095 to about 0.105 inch (2.41 to about 2.67 mm) diameter, and most desirably, the diameter is about 0.100 inch diameter (about 2.54 mm).

Figure 1:
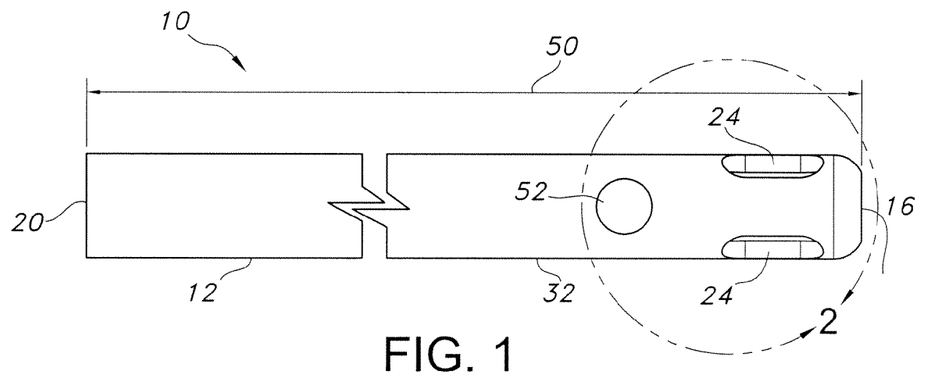
FIG. 1 is a plan view of an atraumatic suction catheter of one embodiment.
Figure 2:
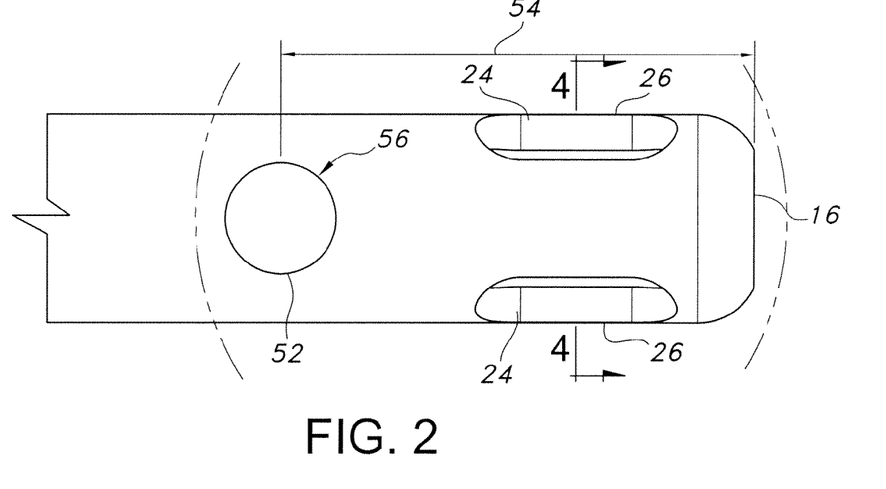
FIG. 2 is sectional view of FIG. 1 taken at line 2.
Figure 3:
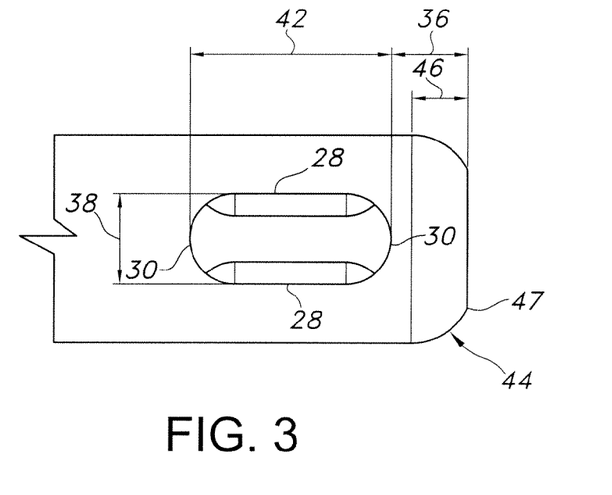
FIG. 3 is a sectional view similar to FIG. 2, showing the detail of one of the openings near the distal tip of the catheter.
Figure 4:
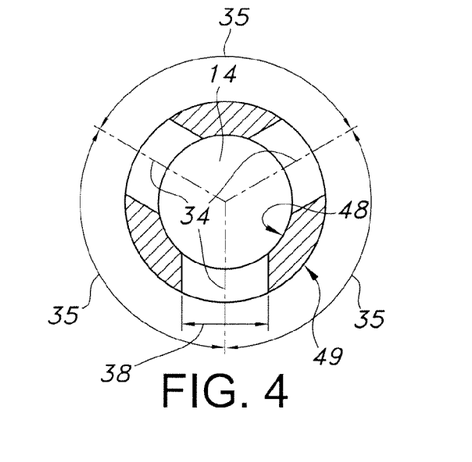
FIG. 4 is a cross-sectional view of FIG. 2 taken along lines 4-4.
Figure 5A:
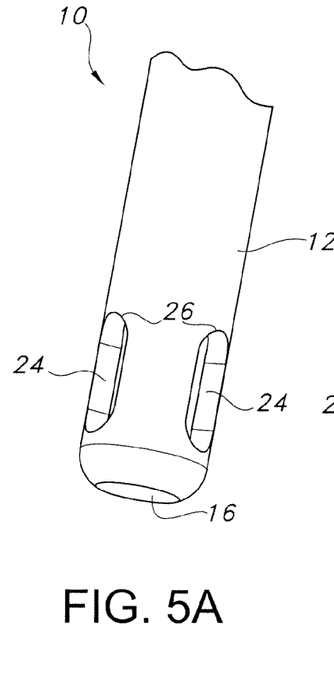
FIG. 5A is a perspective view of the distal tip of FIGS. 1-3.
Figure 5B:
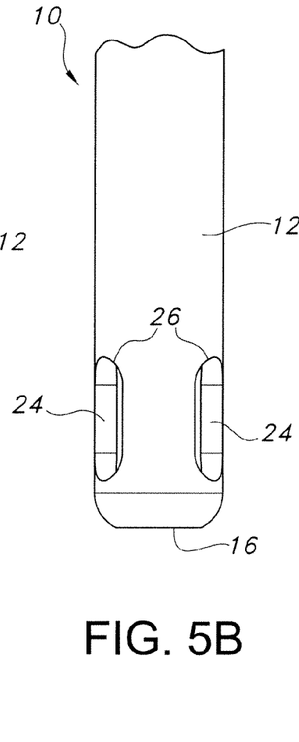
FIG. 5B is a side view of the distal tip of FIGS. 1-3.
Figure 5C:
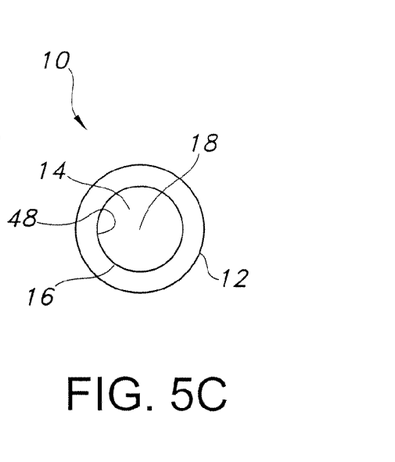
FIG. 5C is a plan view of the distal tip of FIGS. 1-3.
Figure 6A:
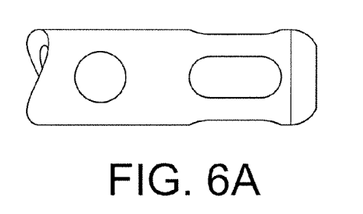
FIG. 6A is a perspective view of the tip of an embodiment of another atraumatic suction catheter having four racetrack shaped apertures.
Figure 6B:
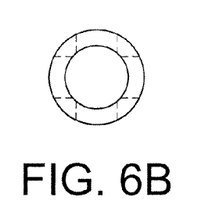
FIG. 6B is a cross-sectional view of the tip of FIG. 6A.
Figure 6C:
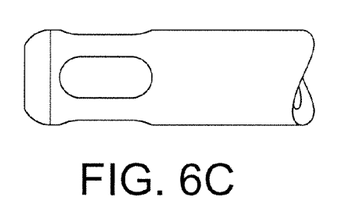
FIG. 6C is a perspective view of the opposite side of the tip of FIG. 6A.
Figure 7A:
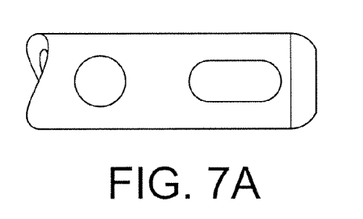
FIG. 7A is a perspective view of the tip of an embodiment of another atraumatic suction catheter having two racetrack shaped apertures.
Figure 7B:
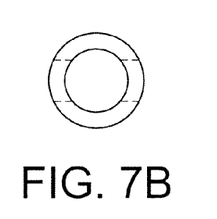
FIG. 7B is a cross-sectional view of the tip of FIG. 7A.
Figure 7C:
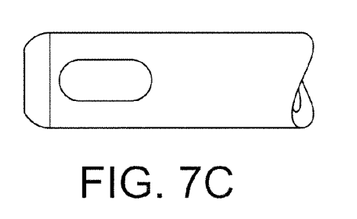
FIG. 7C is a perspective view of the opposite side of the tip of FIG. 7A.
Figure 8A:
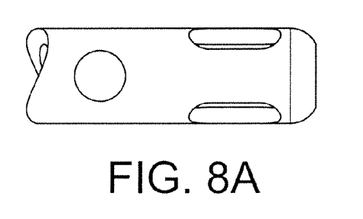
FIG. 8A is a perspective view of the tip of an embodiment of another atraumatic suction catheter having three racetrack shaped apertures.
Figure 8B:
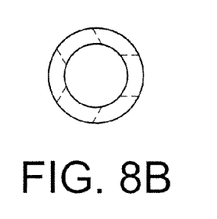
FIG. 8B is a cross-sectional view of the tip of FIG. 8A.
Figure 8C:
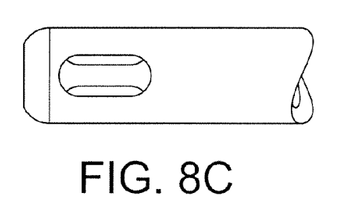
FIG. 8C is a perspective view of the opposite side of the tip of FIG. 8A.
Figure 9A:
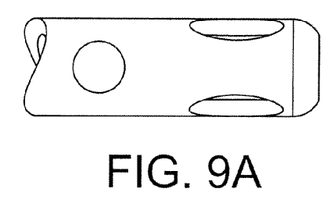
FIG. 9A is a perspective view of the tip of an embodiment of another atraumatic suction catheter having three oval shaped apertures.
Figure 9B:
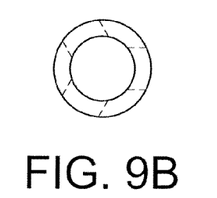
FIG. 9B is a cross-sectional view of the tip of FIG. 9A.
Figure 9C:
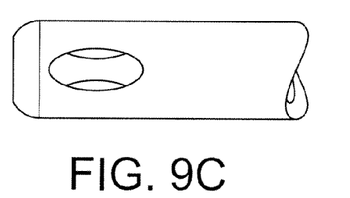
FIG. 9C is a perspective view of the opposite side of the tip of FIG. 9A.
Figure 10A:
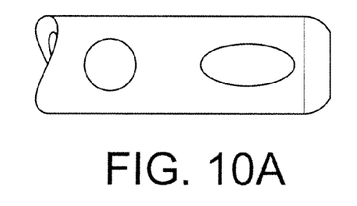
FIG. 10A is a perspective view of the tip of an embodiment of another atraumatic suction catheter having two oval shaped apertures.
Figure 10B:
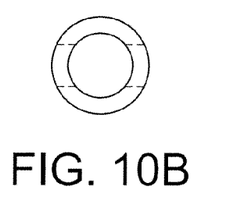
FIG. 10B is a cross-sectional view of the tip of FIG. 10A.
Figure 10C:
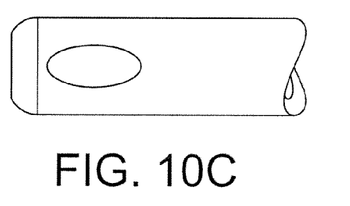
FIG. 10C is a perspective view of the opposite side of the tip of FIG. 10A.
Figure 11A:
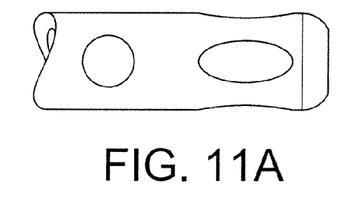
FIG. 11A is a perspective view of the tip of an embodiment of another atraumatic suction catheter having four oval shaped apertures.
Figure 11B:
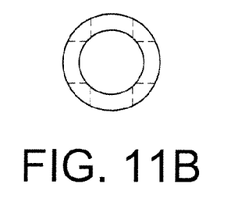
FIG. 11B is a cross-sectional view of the tip of FIG. 11A.
Figure 11C:
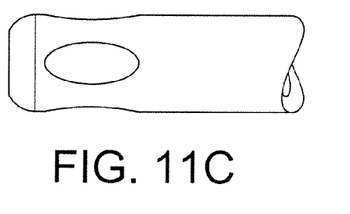
FIG. 11C is a perspective view of the opposite side of the tip of FIG. 11A.

The suction catheter 10 may be made from one or more relatively soft polymers like thermoplastic polyurethane elastomers, thermoplastic polyolefin elastomers, thermoplastic polyolefin block copolymers, SBS di-block elastomers, SEBS tri-block elastomers, polyvinyl chloride, polyethylene terephthalate and blends and mixtures thereof. A particularly suitable polymer is a phthalate-free polyvinylchloride (PVC) available from Colorite Polymers (Ridgefield, N.J.) under the designation 8888G-01 SF. The relative hardness of the polymer used to make the catheter may be measured by the Shore hardness, a series of scales that is known to those skilled in the art. Hardness is measured using a device called a "durometer", an instrument specifically developed to measure relative hardness, and is usually performed following ASTM D2240. In the Shore A and D hardness or durometer scales, a higher number indicates a polymer that is harder than a polymer having a lower number within each scale. The Shore A and D scales are used for different types of polymers. Typically the Shore A scale is used for softer, more elastic polymers and the Shore D scale used for stiffer polymers. When comparing the Shore A and Shore D scales, low D values are typically harder than high A values. For example, a polymer having a 55 D hardness is typically harder than one having a 90 A shore hardness value. Desirably, the suction catheters disclosed herein may have a Shore hardness between 55 A and 90 A One embodiment, as shown and described in FIGS. 1-4, 5A-5C and 8A-8C will be referred to below as the "three hole racetrack design" suction catheter 10, because of its three lateral apertures 24 and their racetrack shape. The Other embodiments include a 2-hole racetrack design (FIG. 7A-7C), a 4-hole racetrack design (FIG. 6A-6C), a three hole oval design (FIG. 9A-9C), a two hole oval design (FIG. 10A-100), a four hole oval design (FIG. 11A-11C), a three hole hexagon design and a three hole square design. The total area of all of the lateral apertures 24 of each of the designs of these embodiments is desirably substantially the same.

Figure 13A:
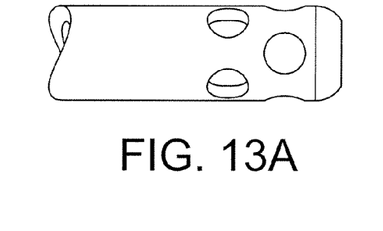
FIG. 13A is a perspective view of the tip of an embodiment of another atraumatic suction catheter having an off-set double row of four holes each.
Figure 13B:
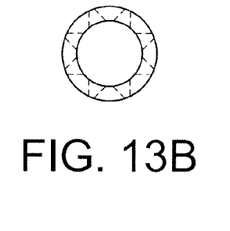
FIG. 13B is a cross-sectional view of the tip of FIG. 13A.
Figure 13C:
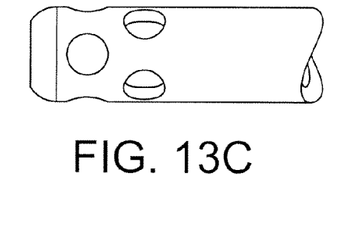
FIG. 13C is a perspective view of the opposite side of the tip of FIG. 13A.

Another embodiment, a multilevel hole design having four equally spaced holes on one level and another four equally spaced holes at another level, offset so the centerline of the holes of one level falls between the centerline of the holes of the other level, is shown in FIG. 13. For purposes of the ratio calculation below, the relevant area is the circumference of the catheter multiplied by the distance from the top of the proximal hole to the bottom of the distal hole.

The total area of the apertures 24 may be expressed as a ratio with the relevant area of the outer surface of the catheter 10. The relevant area of the outer surface of the catheter is that around the catheter and from the top of the apertures 24 to the bottom, i.e. between the two opposing rounded ends 30. The ratio of open aperture area to total relevant area of the catheter is desirably between 28 and 42 percent, more particularly between 32 and 39, and still more particularly about 38 percent.

Comparative Examples

Figure 12A:
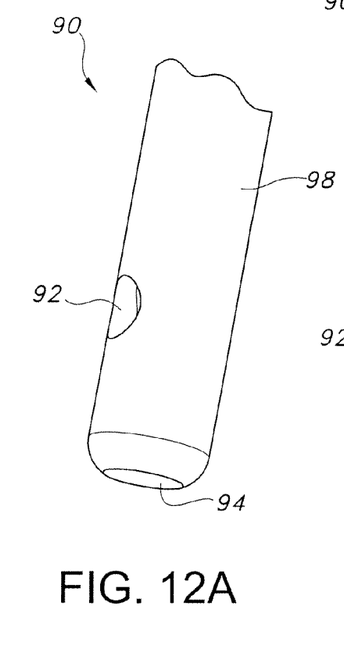
FIG. 12A is a perspective view of the tip of a commercial suction catheter.
Figure 12B:
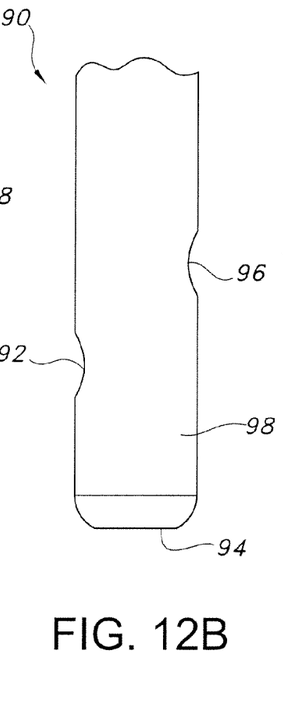
FIG. 12B is a side view of the tip of FIG. 12A.
Figure 12C:
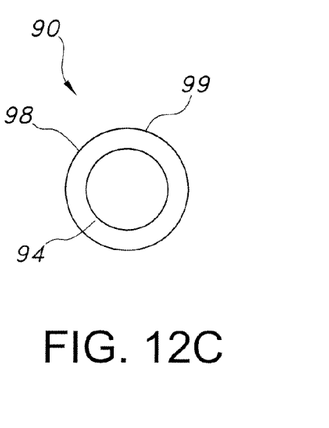
FIG. 12C is a plan view of the tip of FIGS. 12A and 12B.

Current Kimberly-Clark commercial design (off set holes): a suction catheter 90 illustrated in FIGS. 12A-12C made from the same material as the present embodiment, and which has the same construction and generally identical to the 2-hole circular design, except that the suction catheter 90 has a distal hole 92 desirably positioned about 0.25 inch (about 6.35 mm) from the distal tip 94, and a second, proximal hole 96 which is positioned about 180 degrees away from the distal hole 92 on an opposite side of a perimeter 97 of the Off-Set Hole suction catheter 90, and which is spaced about 1.75 inch (about 44.45 mm) from the distal tip 94. The inner diameter 98 of the catheter is desirably about 0.128 inch (about 3.25 mm): the outer diameter 99 of the catheter is desirably about 0.184 inch (about 4.67 mm). This catheter may be found on products available under the trade names TRACH CARE® from BALLARD® Medical Products and KIMVENT®, all from Kimberly-Clark Corporation and is used in a "closed suction catheter" system where the catheter remains within a plastic bag except for when it is used to suction secretions from the respiratory tract of a patient.

A suction catheter is available from Covidien Ltd. of the Republic of Ireland (US headquarters in Mansfield Mass.) under the trade name Ty-Care® exel suction catheter. This catheter has four equally spaced small circular apertures arranged around the circumference of the catheter, all at the same distance from the tip.

The following table contains measurements of the area of the apertures, relevant area and the ratio according to the calculation set forth above. All catheters were 14 French except the Covidien design which was 16 French. While there may be some variation in the ratio due to French size of the catheter, it is believed this will be minimal and that these results will be similar at different French sizes.

| | Aperture area (mm) | Relevant area (mm) | Ratio |
|---|---|---|---|
| Two hole racetrack | 23.87 | 66.77 | 0.357 |
| Three hole racetrack | 25.16 | 66.77 | 0.377 |
| Four hole racetrack | 25.80 | 66.77 | 0.386 |
| Two hole oval | 21.93 | 66.77 | 0.329 |
| Three hole oval | 24.19 | 66.77 | 0.362 |
| Four hole oval | 21.93 | 66.77 | 0.329 |
| Three hole hexagon | 21.68 | 66.77 | 0.325 |
| Three hole square | 27.87 | 66.77 | 0.417 |
| Three hole teardrop | 21.1 | 66.77 | 0.316 |
| Multilevel holes | 25.80 | 66.77 | 0.386 |
| Current KC Commercial | 10.19 | 100.51 | 0.101 |
| Covidien design | 5.81 | 28.97 | 0.200 |

Finite Element Analysis

Finite element analysis (FEA) was conducted for each of the above-referenced designs.

Peak Contact Stress FEA:

The initial FEA was conducted on the 3-hole racetrack, current commercial design (2 offset holes) and a preliminary design that consisted of 2 equally sized holes placed directly across from one another on either side of the catheter tip. All catheters were 14 French. The FEA was conducted to assess the peak contact stresses that were exerted on the surface of the tracheal tissue. Each catheter was held about 0.797 inch (about 20.24 mm) from the distal tip, and the tip of each catheter was positioned about 0.797 inch above a simulated tracheal model. Each catheter had a 0.5 lb (2.22 N) force applied axially with a uniform distribution onto the simulated tracheal model (mesh). Certain features of the tracheal tissue, 60 A hardness PVC and 78 A hardness PVC are outlined below. Tracheal properties are from *Strength of Biological Material* by Hiroshi Yamada, published by Robert E. Krieger Publishing Company, Huntington, N.Y. 1973, p. 141-142. The PVC properties referenced were preliminary values obtained from Matweb.

Material Characteristics

| | Tracheal Tissue | 60A PVC | 78A PVC |
|---|---|---|---|
| Tensile Strength | 341.36 psi | 1600 psi | 2300 psi |
| Elastic Modulus | 2702.34 psi | 550 psi | 1200 psi |
| Poisson's Ratio | — | 0.3 | 0.3 |
| Yield Strength | — | 1600 psi | 2300 psi |

A mesh was utilized to model tracheal tissue, as follows:

| Mesh Type: | Solid Mesh/Standard: |
|---|---|
| Jacobean Check | 16 Points |
| Element Size | 0.04549 inch |
| Tolerance | 0.0022745 inch |
| Number of Elements | 71177 |
| Number of Nodes | 111786 |

Restraints were located on 2 fixed faces of the tracheal model. Force applied was 0.5 lbs (2.22 N) applied along an axial alignment with respect to each distal tip of each design with uniform distribution. Contact set: touching faces, but no penetration between the selected tracheal model and the selected design tip. The program used was CosmosWorks 2008 which is associated with SolidWorks 2008 SP3.1.

The term "peak tip stress" (measured in psi) as used in herein and documented in Table 1 means the peak stress distributed within the tip. The term "peak contact stress" (measured in psi) as used herein and documented in Table 1 means the stress distributed to the tracheal tissue.

The three hole racetrack and the two hole oval designs performed comparably or slightly better than the commercial design, according to the results shown in Table 1. Forces that might be expected due to the advancement of a distal end of a catheter to a carina as well as the effect of catheter hardness (i.e., 78 A, 72 A or 60 A) were determined. The FEA simulations were again tested on each design, using 0.2 lbs (0.89 N), 0.5 lbs (2.224 N) and 1 lb (4.45 N) force, and the resulted are noted below in Table 1.

TABLE 1

| Peak Contact Stress | | |
|---|---|---|
| | psi | Kgf/cm2 |
| 3-hole racetrack - 78A (0.2 lb insertion force) | 49 | 3.45 |
| 3-hole racetrack - 78A (0.5 lb insertion force) | 110 | 7.73 |
| 3-hole racetrack - 78A (1.0 lb insertion force) | 175 | 12.30 |
| 3-hole racetrack - 60A (0.2 lb insertion force) | 34 | 2.39 |
| 3-hole racetrack - 60A (0.5 lb insertion force) | 99 | 6.96 |
| 3-hole racetrack - 60A (1.0 lb insertion force) | 171 | 12.02 |
| 2-hole circular - 78A (0.2 lb insertion force) | 49 | 3.45 |
| 2-hole circular - 78A (0.5 lb insertion force) | 135 | 9.49 |
| 2-hole circular - 78A (1.0 lb insertion force) | 198 | 13.92 |
| 2-hole circular - 60A (0.2 lb insertion force) | 49 | 3.45 |
| 2-hole circular - 60A (0.5 lb insertion force) | 120 | 8.44 |
| 2-hole circular - 60A (1.0 lb insertion force) | 148 | 10.41 |
| Commercial - 78A (0.2 lb insertion force) | 50 | 3.52 |
| Commercial - 78A (0.5 lb insertion force) | 134 | 9.42 |
| Commercial - 78A (1.0 lb insertion force) | 210 | 14.76 |

The results from Table 1 illustrate that the three hole racetrack design performs similarly to the commercial design at low insertion forces (0.2 lbs), but had lower peak contact stress at higher insertion forces, which appears to be due to the shock-absorbing nature of the design. Notably, the variation in polymer hardness did not impact the results of the three hole racetrack design compared to the other designs, the improvement in peak contact force appeared to be obtained by geometry alone.

The two hole circular design performed similarly when compared to the commercial design and the three hole racetrack design. The concern with this catheter design, however, was that at a lower hardness, the catheter collapses to an extent which may block or significantly effecting suctioning.

Maximum Displacements FEA

FEA was completed to observe the nature of buckling and the maximum and minimum displacements for various tip design configurations. Material Characteristics (supplied from Colorite Polymers)

|  | 78A PVC |
|---|---|
| Tensile Strength | 2399 psi (16547400 N/m^2) |
| Elastic Modulus | 870.22 psi (6000000 N/m^2) |
| Poisson's Ratio | 0.47 |
| Yield Strength | 1000 psi (6894760 N/m^2) |
| FEA Mesh Type: | Solid Mesh/Standard: |
| Jacobean Check | 4 Points |
| Global Size | 0.01499 inch (0.00038 m) |
| Tolerance | 0.00075 inch (1.905e−005 m) |

The catheter was analyzed independent of the contact surface. The global contact set was set to bonded. A fixed restraint was placed on the distal surface of the catheter tip. A fixed restraint was placed on 0.25 in (6.35 mm) of the proximal cylindrical face of the catheter with zero radial and circumferential translation. Force (0.5 lb and 0.8 lbs) (2.224 N and 3.559 N) was applied along an axial alignment with respect to each distal tip of each design with uniform distribution. The program used was Simulation 2009 which is associated with SolidWorks 2009.

The following four designs were evaluated using finite element analysis: two hole racetrack, three hole racetrack, four hole racetrack, and three hole oval. The various racetrack designs had lateral apertures equivalent in total area distributed in configurations of two, three, and four around a 14 French catheter tip. The apertures of the oval design were equivalent in length and width to the three hole racetrack design but formed an elliptical configuration, also 14 French.

The catheter tips were analyzed to gain information regarding the buckling pattern. The analyses also provided the resultant displacements in the X and Y directions while the catheter was subjected to static Z-directional loads of 0.5 lb and 0.8 lbs (2.224 N and 3.559 N). The FEA studies provided an initial static comparison of the individual catheters without introducing buckling upon contact. The analyses did not consider the stress relaxation of the material. The results are shown in Table 2 below.

TABLE 2

| FEA Solver | Tip Configuration | Input Force | UX | UY |
|---|---|---|---|---|
| Simulation | 2-hole Racetrack | .8 lbf (3.559 N) | .036 in (.00091 m) | .156 in (.00396 m) |
| Simulation | 4-hole Racetrack | .8 lbf (3.559 N) | .006 in (.00015 m) | .140 in (.00356 m) |
| Simulation | 3-hole Racetrack | .8 lbf (3.559 N) | .014 in (.00036 m) | .133 in (.00338 m) |
| Simulation | 3-hole Hexagon | .8 lbf (3.559 N) | .014 in (.00036 m) | .140 in (.00356 m) |
| Simulation | 3-hole Square | .8 lbf (2.224 N) | .012 in (.00030 m) | .145 in (.00368 m) |
| Simulation | 3-hole Oval | .8 lbf (3.559 N) | .015 in (.00038 m) | .138 in (.00351 m) |

The three hole racetrack design was tested as the control and it was observed that all of the cross-members of the apertures buckled outwardly. The results showed that the two hole racetrack design did not buckle in the preferred manner. The two hole racetrack design, upon buckling, allowed for occlusion of the tip and displacements in both the X and Y directions that were much greater than the control. The displacements for the 4-hole racetrack design were much less than the control in the X direction but since the areas of the individual lateral apertures 24 were much smaller than the control, problems associated with clogging during suctioning may occur. The displacements for the 3-hole oval design were similar to the control; slightly greater than the control at higher loads, but still fell within an acceptable range.

The three hole configurations were analyzed at the worst case loading of 0.8 lbf: three hole racetrack, three hole oval, three hole square, and three hole hexagon. The displacements for the three hole hexagon were slightly greater than the control. The Y displacements for the three hole square were greater than the control but fell between the extremes of the two hole and four hole configurations.

It was determined that by adjusting the geometry of the tip design, a reduction in the applied force was obtained. This is significant because other manufacturers have attempted to reduce applied force by adjusting the hardness of a suction catheter distal tip to make it softer. In doing so, however, the softer distal tip often collapses, buckles inwardly and blocks the central lumen, significantly effecting suctioning efficiency. The disclosed embodiments avoid this problem. In fact, it was found that the 3 hole designs generally buckled outwardly when coming in contact with an object and did not occlude the tip even when the impact of the catheter tip with the surface of the object was not perpendicular.

Suction Efficiency Testing

Suction efficiency testing was also performed on the designs. The testing was based on an article by Shah, Samir, Kung, Kevin, et al., *An In Vitro Evaluation of the Effectiveness of Endotracheal Suction Catheters*, Chest 2005; 128:3699-3705. The testing used an A-Vac Industries vacuum pump (DV-4E 4CFM), a Control Air Inc. pressure regulator (0-15 psi range), a vacuum chamber with a pressure gauge, (Ohaus Adventurer Pro Scale Model AV81011, 1-019), a Brookfield Digital Viscometer (LVTDV-II), and Polyox water soluble resin coagulant from the Dow Chemical Company.

The vacuum pump was connected to the pressure regulator. The pressure regulator was connected to the vacuum chamber. The catheter design being tested was connected to the vacuum chamber. All connections were evaluated to ensure they were air tight and UV curable Loctite glue was added to appropriate connection on the vacuum chamber to ensure sealing.

Appropriate amounts of polyethylene oxide and water were weighed in separate beakers and set aside to make concentrations of 0.5%, 1.5% and 3% polyethylene oxide to water to simulate mucous at three different viscosities. Each beaker containing water was placed in a water bath or on a heating plate until the water temperature was 95 degrees Celsius. The Polyox powder was added to the water and the combined solution was stirred continuous, then removed from the heat source. The mixtures sat for two hours to bring them to room temperature and were stirred periodically.

The test was conducted by attaching the catheter being tested to the vacuum chamber and ensuring that all connections were air tight. All catheters were 14 French. Each catheter tested was supported and the distal end of the catheter was inserted vertically until it was submerged into the polyethylene oxide water solution. The vacuum was turned on and the pressure regulator was observed until the pressure gauge read the appropriate value inside the vacuum chamber. The scale was zeroed. Suction was applied to the catheter at 120 mm Hg and 300 mm Hg pressure for five seconds for each coagulant mixture. The value on the scale was recorded and the amount of mucous suctioned was reported in grams. The catheter was inserted into water and suction was applied until the catheter was rinsed clean. Three different suction catheter designs were utilized in the test. The tip of each catheter design was completely submerged in the solution, however, the upper aperture was not submerged. The process was repeated for each catheter with five times per design. The amounts in grams of Polyox coagulant solution at three different concentrations, suctioned in five seconds, are provided below in Table 3.

TABLE 3

| Design | 120 mmHg | | | 300 mmHg | | |
|---|---|---|---|---|---|---|
| | 0.5% | 1.5% | 3.0% | 0.5% | 1.5% | 3.0% |
| 3-hole ractrack | | | | | | |
| Average | 5.4 | 3.22 | 0.68 | 11.6 | 6.08 | 2.38 |
| St. Dev. | 1.30 | 0.55 | 0.43 | 1.64 | 0.29 | 1.51 |
| Maximum | 6.5 | 4.2 | 1.2 | 13.7 | 6.3 | 4.7 |
| Minimum | 3.6 | 2.9 | 0.2 | 9.4 | 5.6 | 0.5 |
| 2-hole circular | | | | | | |
| Average | 5.98 | 2.36 | 0.36 | 11.36 | 4.16 | 1.12 |
| St. Dev. | 0.57 | 1.26 | 0.11 | 0.91 | 2.02 | 0.26 |
| Maximum | 6.7 | 4.0 | 0.5 | 12.6 | 6.2 | 1.5 |
| Minimum | 5.4 | 1.2 | 0.2 | 10.2 | 2.2 | 0.8 |
| Commercial | | | | | | |
| Average | 5.82 | 2.12 | 0.3 | 10.5 | 3.24 | 0.22 |
| St. Dev | 0.97 | 1.03 | 0.12 | 0.96 | 0.15 | 0.08 |
| Maximum | 6.7 | 3.9 | 0.5 | 11.8 | 3.4 | 0.7 |
| Minimum | 4.2 | 1.7 | 0.2 | 9.1 | 1.0 | 0.1 |

All concepts performed equivalently at low viscosity as might be expected. As the viscosity of the solutions increased, suction efficiency decreased for all designs. The three hole racetrack design had better suction efficiency when compared to the other designs as the viscosity increased. This was also evident with higher viscosity solutions as the suction pressure was increased from 120 mm Hg to 300 mm Hg. In regards to area to suction, it is noted that the total area of the apertures for the 3-hole racetrack design is 444% compared to a catheter tube with only a distal opening. The commercial 2 off-set hole design has an area of about 228% as compared to the tube with only the distal opening. The 3-hole design has increased side orifices. It is believed that the larger the side hole, the greater the airflow, resulting in a greater suction force being applied to move the coagulant. This effect was only observed at increased viscosity levels when the coagulant was not lodged within the apertures.

Impact Force Testing

The various designs were also subjected to impact force testing. The test was conducted to evaluate the peak force at impact, independent from the surface area but dependent on the rate of insertion.

The impact force test is run by placing an upper load cell on the moveable crosshead of a constant velocity tensile frame. A clamp is attached to the upper load cell that holds the catheter tip. The tip is clamped with 1 inch (25.4 mm) of the catheter exposed below the clamp and perpendicular to the clamp. The catheter will move parallel to the motion of the crosshead.

On lower side of the tensile frame, the fixed side, a second load cell is attached (lower load cell). A strike plate is attached to the lower load cell, orientated to create a flat surface parallel to the upper catheter clamp and perpendicular to the catheter.

The test is run by moving the upper crosshead at a velocity of 0.5 inches/min (12.7 mm/min) toward the lower strike plate until the catheter strikes the lower strike plate. The crosshead will then continue to move downward at the same velocity until a force of 0.5 lbf (2.224 N) is read on the upper load cell. At this point, the crosshead will stop moving. While the crosshead is moving and the catheter is in contact with the lower strike plate, the lower load cell will measure the peak force applied to the lower strike plate, which is the maximum impact load.

The steps were repeated for each design sample in 14 French size, varying the input force and speed as noted herein. Temperature for all tests described herein was about 72 degrees F.+/−2 (22° C.+/−1). Relative humidity was about 45 percent, +/−5 percent. All samples were made from the same material; Colorite Polymers' 7866G-015SF. The results are given below.

Average Impact Forces for Punched Samples:

| Initial Impact Force Data | | | | | |
|---|---|---|---|---|---|
| 3 hole racetrack .5 in/s .1 lbf Peak Load Absorbed (lb) | 3 hole racetrack .5 in/s .5 lbf Peak Load Absorbed (lb) | 3 hole racetrack .5 in/s 1 lbf Peak Load Absorbed (lb) | 3 hole racetrack 1 in/s .1 lbf Peak Load Absorbed (lb) | 3 hole racetrack 1 in/s .5 lbf Peak Load Absorbed (lb) | 3 hole racetrack 1 in/s 1 lbf Peak Load Absorbed (lb) |
| 1.141984 | 1.456704 | 1.627552 | 1.79648 | 1.84576 | 1.82784 |
| KC 2- offset hole .5 in/s .1 lbf Peak Load Absorbed (lb) | KC 2- offset hole .5 in/s .5 lbf Peak Load Absorbed (lb) | KC 2- offset hole .5 in/s 1 lbf Peak Load Absorbed (lb) | KC 2- offset hole 1 in/s .1 lbf Peak Load Absorbed (lb) | KC 2offset hole 1 in/s .5 lbf Peak Load Absorbed (lb) | KC 2- offset hole 1 in/s 1 lbf Peak Load Absorbed (lb) |
| 1.74272 | 2.43712 | 2.58944 | 3.502384 | 3.650752 | 3.884544 |

| .5 in/s stop at 1 lbf | 3-hole racetrack | KC 2- offset holes |
|---|---|---|
| Average Peak | 1.71 lbf (7.638 N) | 2.38 lbf (10.6 N) |

-continued

Initial Impact Force Data

| | | |
|---|---|---|
| Impact Force St Dev | .352 | 1.28 |
| Sample size | 16 | 96 |

Reduction in peak impact forces ranged from 35%-53%.

Average Impact Forces for Laser Cut Samples:

| 12.7 mm/s stop at 1 lbf | no hole, flat tip | 3-hole racetrack | 3-hole Oval | 4-hole racetrack | 3-hole rectangle | 2-hole racetrack |
|---|---|---|---|---|---|---|
| Avg Peak | 2.48 lbf, | 1.22 lbf, | 1.38 lbf, | 1.28 lbf, | 1.08 lbf, | 1.10 or |
| Impact Force | 11.03 N | 5.43 N | 6.154 N | 5.69 N | 4.80 N | completely occludes |
| Sample size | 3 | 2 | 2 | 3 | 3 | 3 |

It can clearly be seen that the catheter with no holes, believed to be analogous to the commercial offset hole design, has a much higher impact force. The designs disclosed herein have an impact force of at least 35 percent less than the no hole design, more particularly at least 45 percent less and still more particularly at least 55 percent less than the no hole design.

As noted above, the geometry of the catheters providing a lower impact force and reduced buckling may be expressed as a ratio of the open aperture area to total relevant area of the catheter, which is desirably between 28 and 42 percent. An alternate way of expressing this is to consider the amount of open aperture area in the band beginning at from about 1 mm to 3 mm from the distal tip of the catheter and extending proximally about 4 to 6 mm (the critical area). The inventors have found that if this desirably 5 mm high band has an open aperture area of between about 28 and 42 percent, the impact and buckling performance will be greatly superior to catheters not having such open area. The band is defined as an area calculated by multiplying the height of the band by the circumference of the catheter.

As will be appreciated by those skilled in the art, changes and variations to the invention are considered to be within the ability of those skilled in the art. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

It should further be noted that the results throughout this document were developed using English units. In the case of any discrepancy between the Metric (SI) units and the English units herein, the English units should be regarded as the primary authority.

What is claimed is:

1. A suction catheter, comprising:
   a generally tube-shaped body having a lumen formed therethrough, an outer surface, a distal tip having an opening therein in communication with the lumen, a proximal end having an opening in communication with the lumen and adapted to be coupled to a suction source, and;
   a plurality of apertures positioned near the distal tip of said body, said apertures having ends and an area, wherein a ratio of the area of the apertures to an area of the outer surface of the catheter between the ends of the apertures is between 32 and 42 percent, and wherein said apertures are separated by cross-members and said cross-members have a width less than 1.54 mm and wherein said cross-members buckle outwardly upon coming in contact with an object.

2. The suction catheter of claim 1 wherein there are three of said apertures.

3. The suction catheter of claim 1 wherein said plurality of apertures are equally spaced around said catheter.

4. The suction catheter of claim 1 wherein said apertures are racetrack shaped.

5. The suction catheter of claim of claim 1 wherein an end of said apertures is positioned a distance between 1.14 and 2.54 mm from said distal tip.

6. The suction catheter of claim 5 wherein said distance from the distal tip to said end of each aperture does not vary by more than 50 percent.

7. The suction catheter of claim 5 wherein said distance from the distal tip to said end of each aperture does not vary by more than 25 percent.

8. The suction catheter of claim 1 wherein said apertures have a length to width ratio of less than 5.

* * * * *